United States Patent [19]

Hellman, Jr.

[11] Patent Number: 4,865,715
[45] Date of Patent: Sep. 12, 1989

[54] ELECTROPHORESIS DEVICE WITH NEAR-VERTICAL GEL PLATES

[75] Inventor: Robert R. Hellman, Jr., Southbury, Conn.

[73] Assignee: Eastman Kodak Co., Rochester, N.Y.

[21] Appl. No.: 323,106

[22] Filed: Mar. 10, 1989

Related U.S. Application Data

[63] Continuation of Ser. No. 187,670, Apr. 28, 1988, abandoned.

[51] Int. Cl.⁴ .................... G01N 27/26; G01N 27/28
[52] U.S. Cl. .............................. 204/299 R; 204/182.8
[58] Field of Search ............. 204/182.8, 299 R, 182.9, 204/180.1

[56] References Cited

U.S. PATENT DOCUMENTS 3,208,929  9/1965  Raymond et al. ............. 204/299 R
3,932,265  1/1976  Hoefer ........................ 204/182.8 X
4,224,134  9/1980  Hoefer et al. ................ 204/182.8 X
4,292,161  9/1981  Hoefer et al. ................. 204/299 R
4,325,796  4/1982  Hoefer et al. ..................... 204/182.8
4,747,919  5/1988  Anderson ................... 204/299 R X

OTHER PUBLICATIONS

Bio-Rad Price List M, 4/87.

Primary Examiner—John F. Niebling
Assistant Examiner—John S. Starsiak, Jr.
Attorney, Agent, or Firm—Dana M. Schmidt

[57] ABSTRACT

There is described an electrophoresis device having a support for a gel plate assembly, and means for clamping such plate assemblies to the support. The support provides a surface that is inclined at an angle of between about 5° and about 10° from the vertical, so that the bottom of the plate is closer to the user than is the top.

3 Claims, 5 Drawing Sheets

ELECTROPHORESIS DEVICE WITH NEAR-VERTICAL GEL PLATES

This is a continuation of application Ser. No. 187,670 filed Apr. 28, 1988, now abandoned.

FIELD OF THE INVENTION

This invention relates to an electrophoresis device, particularly the type that orients the gel plate assembly generally vertically.

BACKGROUND OF THE INVENTION

Electrophoresis sequencers have been provided with a gel plate, usually precisely vertically mounted, and a buffer tank at the top and bottom. On the device called the BRL Model S2, manufactured by Bethesda Research Labs, Gaithersburg, MD, the top buffer tank is part of the support against which the gel plate is clamped. The bottom tank, though removable, provides no significant contribution to holding the gel plate in place. As a result, separate clamping elements have to be individually pulled and/or rotated and released to hold the vertically oriented gel plate from tipping over. Such clamping elements are tedious and time-consuming in their use, particularly if more than four per plate are required. The tedium is enhanced by reason of the fact that, until the clamps are properly secured, the gel plate has to be manually held from tipping over.

Yet another problem with vertically positioned gel plates is that the sample solutions, as they are applied by the operator into the plate, tend to run over the shorter of the two glass plates of the plate assembly. This not only makes application of samples to the assembly tedious, but it also makes interpretation of results difficult. Such running-over has been experienced on devices such as the aforesaid BRL Model S2.

SUMMARY OF THE INVENTION

I have designed an electrophoresis device which avoids the above-noted problems of securing the gel plate assembly. More specifically, I have altered the support so that the gel plate assemblies no longer incur a risk of falling off while they are being clamped in place.

Most specifically, there is provided an electrophoresis device for electrophoretically separating charged compounds, the device comprising at least one support for mounting at least one gel plate assembly in a generally vertical orientation, a pair of buffer tanks for each gel plate assembly, means for mounting the pair of tanks at opposite ends of each gel plate assembly, means for clamping the gel plate assembly to the support, and means for applying a current at the opposite ends of the each plate assembly. The device is improved in that the support comprises a surface in contact with the gel plate assembly, the surface being inclined at an angle from the vertical that is between about 5° and about 10°, the gel plate assembly being mounted on the support so that, when disposed in position for use, the bottom of the gel plate assembly is closer to the user than is the top of the gel plate assembly.

Thus, it is an advantageous feature of the invention that a gel plate assembly can be placed on the device of the invention for clamping, without having to hold it in place while the clamping operation is initiated and completed.

It is another advantageous feature of the invention that sample loading is less likely to cause sample to run over the surface of the gel plate assembly.

Other advantageous features will become apparent upon reference to the following detailed description, when read in light of the attached drawings.

DESCRIPTION OF THE PREFERRED EMBODIMENTS

The electrophoresis device of this invention is hereinafter described in connection with a two-sided, rotatable embodiment with which it is preferred. In addition it is useful regardless of the number of sides, or their associated gel plate assemblies, that are used, and regardless of whether it is rotated. Furthermore, although the means for clamping the gel plate to its support are preferably the buffer tanks themselves, any clamping means can be used with this invention.

Features of the electrophoresis device other than the orientation of support of the gel plate, described herein, include subject matter that is separately claimed in the following commonly owned related applications co-filed with this application by me: "Lockable, Rotating Electrophoresis Device" bearing Ser. No. 187,127, now U.S. Pat. No. 4,800,020; "Improved Gel Plate Assembly for Electrophoresis" bearing Ser. No. 187,668, now U.S. Pat. No. 4,802,969; and "Electrophoresis Device With Removable Buffer Tank" bearing Ser. No. 187,152 now U.S. Pat. No. 4,828,669.

Parts described herein as being "vertical", "horizontal", "up", "bottom" or with similar direction terms, refer to their orientation when in their normal use.

Figure 1:
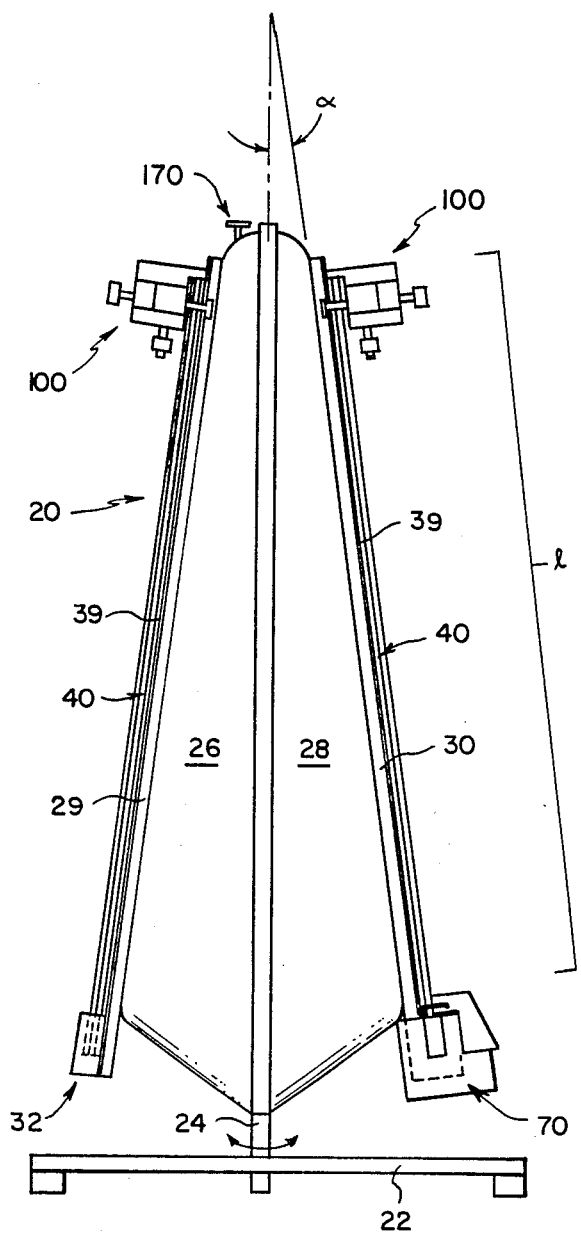
FIG. 1 is an elevational view of an electrophoresis device incorporating the features of the invention.
Figure 2:
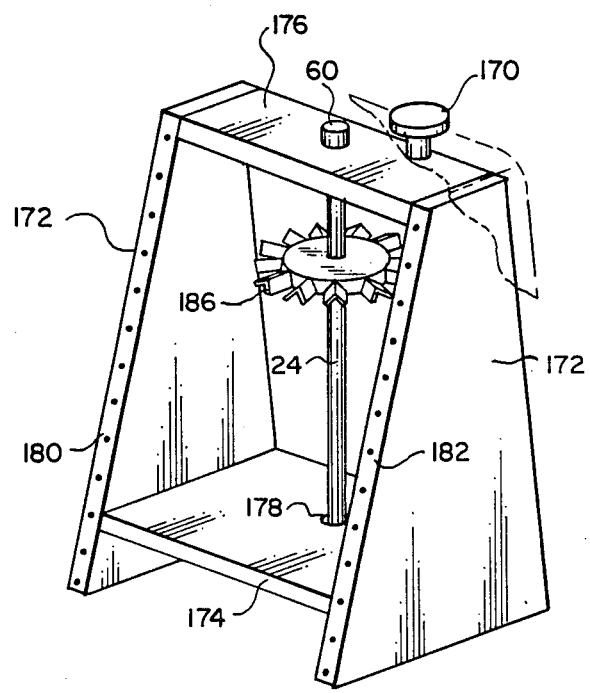
FIG. 2 is a fragmentary isometric view of the interior of the device, partly illustrating the rotatability and lockability of the device.
Figure 3:
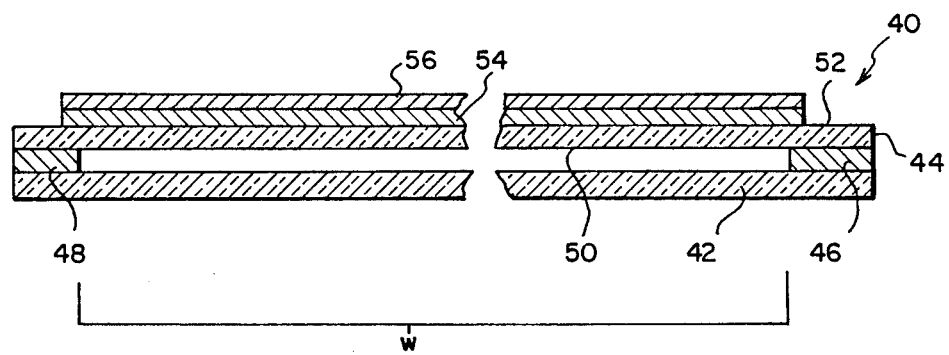
FIG. 3 is a fragmentary sectional view of the gel plate assembly.

An electrophoresis device 20 constructed in accordance with the invention comprises, FIG. 1, a support generally comprising a base 22, a vertical post 24, two clam shell bodies 26, 28 mounted on either side of post 24, and supporting rails 29, 30 providing a support surface for a gel plate assembly 40 that is more completely shown in FIG. 3. Shell bodies 26 and 28 are mounted for rotation, FIG. 2, on post 24, by reason of bushing 60 that rides on the point of post 24. A locking mechanism 170 is provided, effective to releasably hold shells 26, 28 against further rotation. A pair of buffer tanks 70 and 100 are mounted at the bottom of device 20, FIG. 1, and top, respectively, as is conventional. (Only one bottom buffer tank 70 as shown in FIG. 1 for clarity, to allow illustration of trough 32.)

Figure 4:
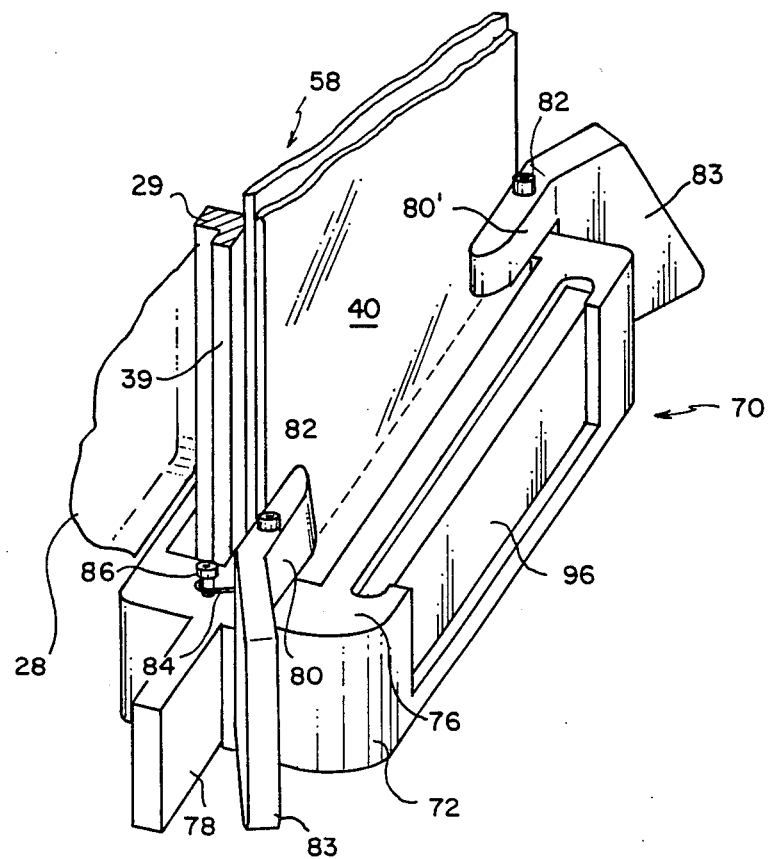
FIG. 4 is a fragmentary isometric view of the bottom buffer tank of the device.
Figure 5:
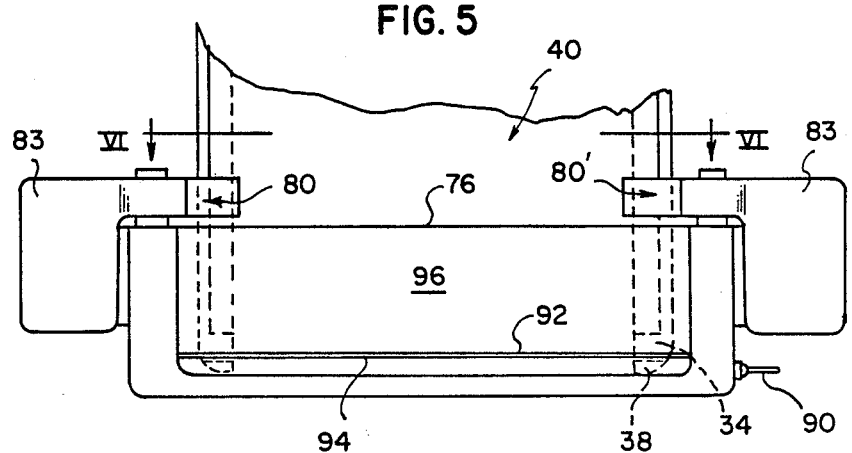
FIG. 5 is a fragmentary front elevational view of the tank of FIG. 4.
Figure 6:
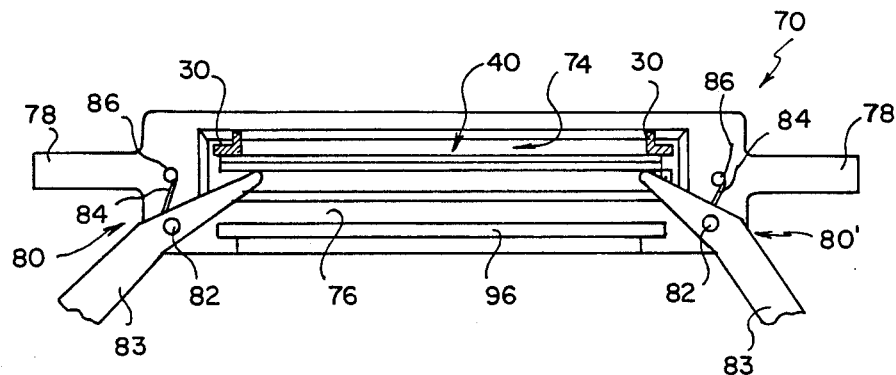
FIG. 6 is a sectional view taken along the line VI—VI of FIG. 5.

Although the supporting surface can be any suitable surface, preferably each of rails 29, 30 is a pair of rails, FIGS. 5 and 6, to provide the supporting surface for gel plate assembly 40. As is seen more clearly in FIGS. 5 and 7, the bottom of each rail features a supporting trough 32 with a front lip 34, that holds gel plate assembly 40 from falling off the rails-see also FIG. 1. Trough 32 in turn comprises a vertical shoulder 36 and a bottom ledge 38. Further, each rail 29, 30 includes a flange 39 that extends the length of the rail, FIGS. 4, 7-8, and 10, to cooperate with clamps for the buffer tanks, as described hereinafter.

Each of the pairs of rails 29 or 30 is associated with its own clam shell. As such, the device permits two electrophoresis gel plate assemblies to be run simultaneously. Alternatively, additional pairs (not shown) can be mounted from the same post, the support being rotated about post 24 until the desired gel plate assembly is facing the operator.

As is conventional, the gel plate assemblies are generally planar, with an extensive height and width that exceed dimensions "l" and "w", respectively, FIGS. 1 and 3. Such plates are relatively thin in the dimension perpendicular to dimensions "l" and "w".

In accord with the invention, the gel plate supporting surfaces comprising the pair of rails is mounted to form an angle α, FIG. 1, that is inclined from the vertical by an amount between about 5° and 10°. As such, the bottom of the gel plate and buffer tank 70 are closer to the operator, when the gel plate faces the operator, than are the top of the gel plate and buffer tank 100. The advantage is that, unlike perfectly vertical plate supports of conventional devices, no care is required to hold the plate on the support while clamps are mounted in place. Instead, the plate is simply inserted into troughs 32, and leaned back aganst rails 29 or 30. The troughs 32 are effective in preventing the plate from dropping lower, and angle α is effective in preventing plate 40 from tipping over, until buffer tanks 70 and 100 are installed.

Angle α is preferably no less than 5°, since otherwise tipping is more likely. It is preferably no greater than 10°, since more than that tends to make the device too bulky at the bottom.

Because the orientation of the gel plate is not precisely vertical, the sample when loaded is less likely to run over the front of the gel plate assembly.

Gel plate assembly 40, FIG. 3, is the entire assembly shown, which comprises a front plate 42, a rear plate 44, and spacers 46, 48 separating the two to allow gel (not shown) to be formed between them, as is conventional. Sample wells are formed at the top of the formed gel, in a conventional manner, using a comb. Preferably, rear plate 44 is improved to insure superior formation and observance of dye lines in electrophoresed samples. That is, plate 44 comprises a front surface 50 and a rear surface 52. Rear surface 52 is preferably coated with a mirroring material 54, such as silver or aluminum, and a layer 56 is bonded over coating 54 to extend in back of the flow surface area of plate assembly 40. As used herein, the bonding of layer 56 "in back of the flow surface area" of the gel plate means, having an extension that is coincident with, and behind, the flow surface area of the gel, wherein the electrophoresis lanes lie. This area is defined by length "l", FIG. 1, and width "w", FIG. 3. Layer 56 is selected from a material that is effective in transferring heat, for example, aluminum. This layer is tightly bonded to coating 54 over substantially all of its surface, by using any suitable means, for example an adhesive such as acrylic adhesive. Preferably, the entire laminate is then overcoated with a protective non-conductive layer.

However, layer 56 is not used to dissipate heat from the gel plate. Rather, the supporting surfaces formed by rails 39 are deliberately held off from body 28 a distance effective to create a dead air space 58, FIGS. 4 and 8. This insulating air space insures that the heat generated by the process remains in place.

Layer 56 is thus effective to transfer heat from the hotter center regions, to the peripheral regions, thereby reducing temperature gradients. As a result, dye lines form in the gel that have the desired straightness, and the results are free of thermally induced artifacts. The overall temperature, however, remains high, thus inducing the dye fronts to progress faster than is the case with water-backed units. That is, the water takes much longer to heat up to operating temperature.

The ability of the dye fronts to be processed substantially free of artifacts remains even when supplying as much as 60 watts of power to achieve temperatures as high as 70° C., when measured at the front of plate 42, producing dye front speeds as high as 0.5 cm/min.

Yet another advantage of such a gel plate is the mirrored surface. This surface insures that the user can more readily tell the condition of surface 50, FIG. 3. That is, the mirrored surface makes it easier to accurately introduce sample solution by pipette into the cavity between plates 42 and 44. It also helps reveal particles of dirt, if any, on surface 50 when plate 44 is being cleaned. The dye lines are also more easily detected with the mirror in place.

Preferably, one or both of the buffer tanks are removable and hence autoclavible. Most preferably, they are releasably mounted by clamping means that not only clamp the box in position, but also clamp the gel plate to the support.

Figure 7:
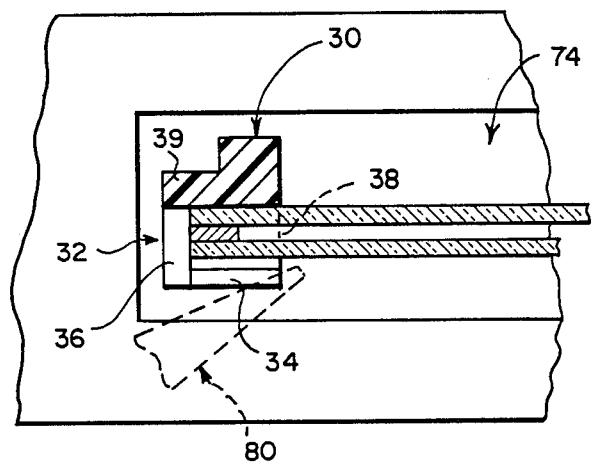
FIG. 7 is a fragmentary enlargement of the portion of FIG. 6 identified as "VII".

With respect to the bottom buffer tank 70, FIG. 4, such tank comprises a cavity 74, FIGS. 6 and 7 open at top surface 76, FIG. 5. The tank has manual grasping ears 78 at either end, and two clamps 80, 80' journalled on post 82 to top surface 76. Each clamp has a handle portion 83. A torsion spring 84 is wrapped around post 82 at one end, FIG. 6, and secured at its other end to a screw 86 attached to surface 76. As a result, clamps 80 and 80' are biased to press inwardly-that is, clamp 80 is biased to rotate counterclockwise, FIG. 6, and 80' to rotate clockwise.

The effect is to not only clamp tank 70 to the support at rails 29, but preferably also to clamp gel plate assembly 40 between the buffer tank and the rails 29. By this construction, it is not necessary that separate clamps or fasteners by used to hold tank 70 in place, apart from those used to clamp the gel plate in place.

Clamps 80 and 80' work by simply grasping the clamp with the thumb and one of the ears with the fingers, and pressing against the torsion spring to release the clamp from contact with the gel plate. This in turn releases the buffer tank from engagement with rails 29 or 30, so that the buffer tank can be removed and cleaned.

As is conventional, a banana plug 90 is mounted at the side of tank 70 for connection to power wires. Inside the tank, plug 90 connects with a wire electrode 92, FIG. 5, that is supported by a rod or tube 94 that extends along the bottom of tank 70. Tube 94 and electrode 92 are preferably removable as a unit.

The front face 98 of tank 70 can be transparent, to aid in viewing the contents thereof.

Similarly, tank 100 can be releasably clamped to the other end of gel plate assembly 40, FIG. 1. Or alternatively, separate clamping means can be used.

The frame by which device 20 rotates comprises, FIG. 2, trapezoids 172 mounted vertically on two horizontal plates 174 and 176. Plate 174 is apertured at 178 to allow post 24 to freely extend through it. Plate 176 provides bushing 60, described hereafter. The outwardly facing edges 180, 182 of each trapezoid 172 provide the mounting support for the pairs of rails mounting on the clam shell bodies, shown in phantom. Bushing 60, FIG. 11, rides on point 184 of post 24. In this fashion, the entire frame comprising plate 174, 176, bushing 60, trapezoids 172 and the attached clam shell bodies and rails, rotates on post 24. Preferably, rotation of the device is temporarily prevented by the locking mechanism 170. Mechanism 170 features a two-position push latch, of a conventional construction, not shown, effective to cause a member to engage or disengage the teeth of a lock plate 186.

The invention has been described in detail with particular reference to preferred embodiments thereof, but it will be understood that variations and modifications can be effected within the spirit and scope of the invention.

What is claimed is:

1. In an electrophoresis device for electrophoretically separating charged compounds, the device comprising at least one support for mounting at least one generally planar gel plate assembly in a generally vertical orientation, a pair of buffer tanks for each gel plate assembly, means for mounting said pair of tanks at opposite ends of each gel plate assembly, means for clamping said gel plate assembly to said support, and means for applying a current at said opposite ends of said each plate assembly;

the improvement wherein said support comprises on each of two opposite sides of said device, a generally planar surface in supporting contact with a generally planar gel plate assembly, each surface being associated with said clamping means for clamping the respective gel plate assembly to said support, each said surface being inclined at an angle from the vertical that is between about 5° and about 10°, said respective gel plate assembly being mounted on said support so that, when disposed in position for use, the bottom of said gel plate assembly is closer to the user than is the top of said gel plate assembly, whereby two separate and independent planar gel plate assemblies are mounted on said device at the same time, in a non-vertical arrangement.

2. A device as defined in claim 1, wherein said support surface comprises a pair of rails.

3. A device as defined in claim 1 or 2, wherein said support surface includes a trough at the lower end thereof constructed to receive and support the lower edge of said gel plate.

* * * * *

UNITED STATES PATENT AND TRADEMARK OFFICE
CERTIFICATE OF CORRECTION

PATENT NO. : 4,865,715

DATED : September 12, 1989

INVENTOR(S) : Hellman, Jr., Robert R.

It is certified that error appears in the above-identified patent and that said Letters Patent is hereby corrected as shown below:

Column 4, line 50 "by" should read "be"

Signed and Sealed this

Thirtieth Day of October, 1990

*Attest:*

HARRY F. MANBECK, JR.

*Attesting Officer*  *Commissioner of Patents and Trademarks*